United States Patent [19]

Murtha et al.

[11] 4,171,245

[45] Oct. 16, 1979

[54] EXTRACTIVE DISTILLATION WITH HYDROCARBON SOLVENT OF MIXTURE OF HYDROCARBYL AROMATIC COMPOUND, HYDROXY AROMATIC COMPOUND AND CARBONYL COMPOUND

[75] Inventors: Timothy P. Murtha; Ernest A. Zuech, both of Bartlesville, Okla.

[73] Assignee: Phillips Petroleum Company, Bartlesville, Okla.

[21] Appl. No.: 802,228

[22] Filed: Jun. 1, 1977

[51] Int. Cl.$^2$ .............................................. B01D 3/40
[52] U.S. Cl. ........................................ 203/68; 203/69
[58] Field of Search ................ 203/68, 69; 260/586 P, 260/621 C, 610 B

[56] References Cited

U.S. PATENT DOCUMENTS

| | | | |
|---|---|---|---|
| 3,497,561 | 2/1970 | Gelbein | 260/621 C |
| 4,019,965 | 4/1977 | Fozzard | 260/586 P |
| 4,021,490 | 5/1977 | Hudson | 260/621 C |
| 4,036,890 | 7/1977 | Ester et al. | 260/610 B |

*Primary Examiner*—Hiram H. Bernstein

[57] ABSTRACT

Acid catalyzed cleavage products of hydrocarbyl aromatic hydroperoxides are subjected to extractive distillation employing a hydrocarbon solvent. In a specific embodiment a mixture containing cyclohexylbenzene, phenol and cyclohexanone obtained from the acid catalyzed cleavage of cyclohexylbenzene hydroperoxide is subjected to extractive distillation employing hexadecane.

8 Claims, 1 Drawing Figure

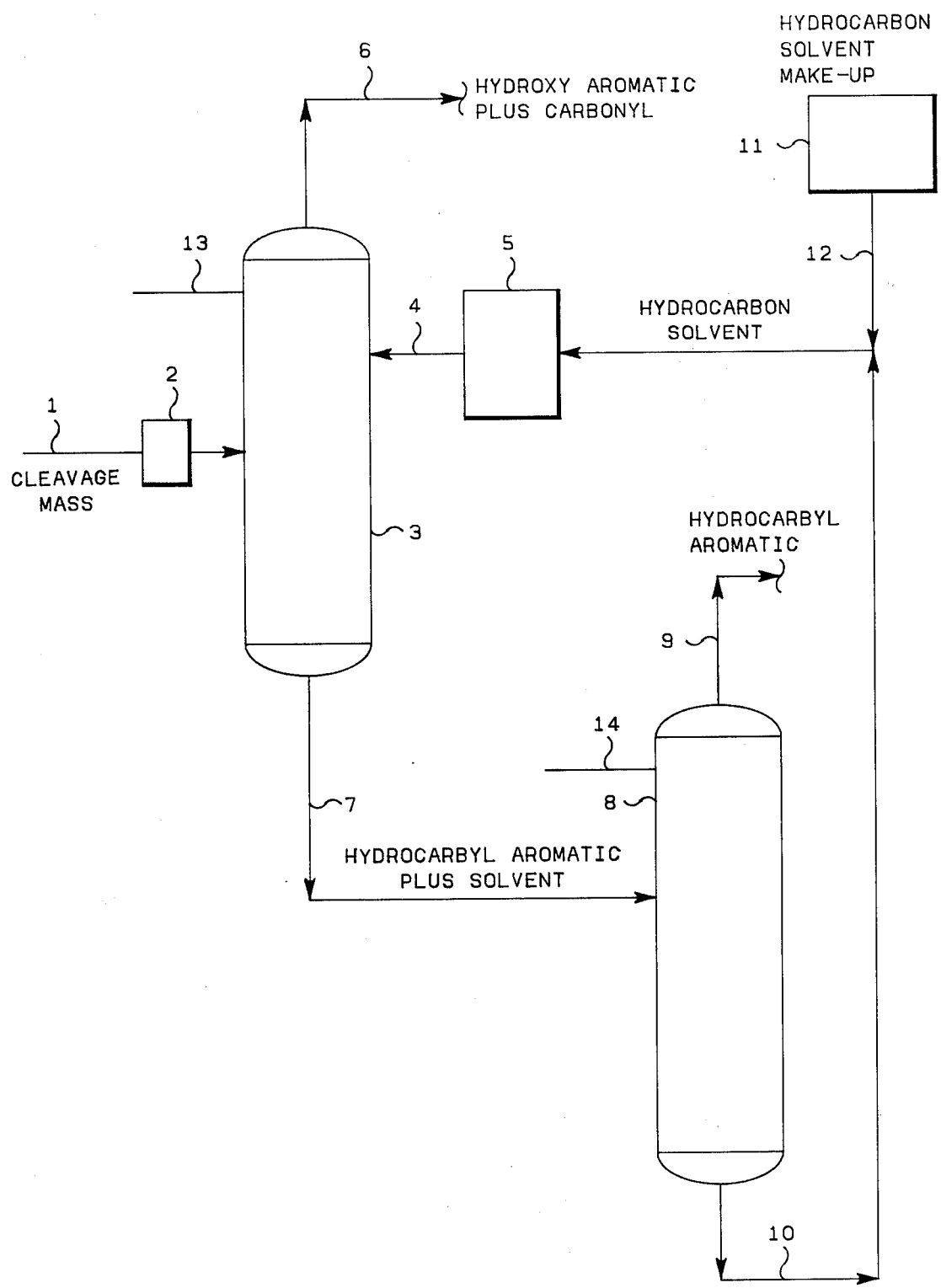

EXTRACTIVE DISTILLATION WITH HYDROCARBON SOLVENT OF MIXTURE OF HYDROCARBYL AROMATIC COMPOUND, HYDROXY AROMATIC COMPOUND AND CARBONYL COMPOUND

This invention relates to extractive distillation. More specifically, it relates to separation of a mixture obtained upon acid catalyzed cleavage of an oxidation product of a hydrocarbyl aromatic compound. Still more specifically, a hydrocarbon solvent is employed for the extractive distillation.

In one of its concepts, the invention provides extractive distillation method for the separation of a mixture obtained upon acid catalyzed cleavage of an oxidation product of a hydrocarbyl aromatic compound employing in the method a hydrocarbon solvent. In another of its concepts, the invention provides a combination of steps in which the cleavage mass is contacted with the solvent in an extractive distillation zone providing an overhead essentially containing hydroxy aromatic compound and carbonyl compound, which can be separated in a further suitable separation step, and a bottoms fraction containing hydrocarbyl aromatic compound and solvent; the bottoms fraction then being introduced into a fractional distillation zone obtaining overhead hydrocarbyl aromatic compound and solvent as bottoms, which can be recycled.

A further concept of the invention provides as hydrocarbon solvent various types of hydrocarbons, e.g., saturated aliphatic, unsaturated cyclic and substituted ring and substituted chain compounds containing points of unsaturation.

Cyclohexylbenzene can be converted to phenol and cyclohexanone via cyclohexylbenzene hydroperoxide. The acid catalyzed cleavage of cyclohexylbenzene hydroperoxide in presence of unoxidized cyclohexylbenzene results in a mixture of cyclohexylbenzene, phenol, and cyclohexanone. This mixture can only be partially separated by fractional distillation. The instant invention provides a method of separating cyclohexylbenzene from a mixture of cyclohexylbenzene, phenol, and cyclohexanone or a mixture of cyclohexylbenzene and phenol. P An object of this invention is to provide an extractive distillation operation. Another object of the invention is to provide an extractive distillation operation suitable for the separation of a reaction mixture obtained upon acid catalyzed cleavage of an oxidation product of a hydrocarbyl aromatic compound. A further object of the invention is to provide a method for the separation of a mixture containing cyclohexylbenzene, phenol, and cyclohexanone. A still further object of the invention is to provide a solvent for such a separation.

Other aspects, concepts, objects and the several advantages of the invention are apparent from a study of this disclosure, the drawing and the appended claims.

According to the present invention, there is provided a method for the extractive distillation separation of a reaction mass obtained upon the acid catalyzed cleavage of an oxidation product of a hydrocarbyl aromatic compound which comprises employing a hydrocarbon solvent.

The instant invention is applicable to the treatment of the product mixture from the acid catalyzed cleavage of oxidation products obtained by the oxidation of hydrocarbyl aromatic compounds having up to 30 carbon atoms and the general formula

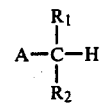

wherein $R_1$ and $R_2$ are either a hydrogen, an alkyl, or an aryl group or wherein $R_1$ and $R_2$ taken together form a cycloalkyl ring having from 4 to 7 carbon atoms; wherein A is an aryl or substituted aryl group, with the substituent groups being one or more of a mixture of alkyl, alkoxy, halogen, nitro, cyano, or the like; and wherein the boiling points of the oxidation substrate is above about 190° C. at atmospheric pressure. The aryl group A may be either mononuclear, i.e., phenyl, or polynuclear, i.e., naphthyl, and the like. Specific examples of suitable compounds to be oxidized for use in the instant invention include amylbenzene, p-diisopropylbenzene, p-methoxy isopropylbenzene, p-chloro isopropylbenzene, p-nitro isopropylbenzene, p-cyano isopropylbenzene, cyclohexylbenzene, cyclopentylbenzene, cycloheptylbenzene, diphenyl methane, 1-ethylnaphthalene, 1-isopropylnaphthalene, 1-cyclohexylnaphthalene, 1-(1-naphthyl)octadecane, 1-(2-naphthyl)octadecane, 1-(1-naphthyl)eicosane and the like.

Compounds represented in the above general formula are oxidized using conditions suitable for the oxidation of the compound used. Such conditions are generally available in the art.

The oxidation reaction can be conducted with air, pure oxygen, or mixtures of oxygen with inert gases using known methods. This invention is applicable to separation of mixtures obtained employing suitable oxidation initiators or catalysts. As known the oxidation reaction mixture separated can be obtained in the presence of suitable amounts of base to neutralize acidic materials which may be formed as by-products in the oxidation reaction. The crude oxidation product is generally filtered to remove insoluble salts which may have formed.

According to the instant invention, the method used for the hydroperoxide cleavage is not critical. Any method known in the art can be employed. For example, strong protonic acids such as sulfuric acid, arylsulfonic acids, e.g., p-toluenesulfonic acid, trifluoroacetic acid, and the like can be used for the cleavage of the hydroperoxide.

The hydroperoxide cleavage product is treated in a manner that is suitable for the method of cleavage used. For example, if a strong protonic acid is used for the hydroperoxide cleavage, there will generally be an aqueous phase and an organic phase at the conclusion of the cleavage reaction. If there is only one phase present, suitable amounts of water can be added to form a separate aqueous phase containing most of the strong acid peroxide cleavage catalyst and an organic phase containing essentially all of the cleavage products, which are not appreciably soluble in water. The aqueous phase is separated and the remaining organic phase is neutralized with a suitable amount of base such as an alkali metal hydroxide or carbonate or an alkaline earth metal hydroxide or carbonate. The amount of neutralizing base employed will at least be that amount to neutralize the acid present in the organic phase. Generally an excess of that amount required for this neutralization is employed for the convenience in speeding up the neutralization reaction. The organic phase, which has been treated with base to neutralize the acid present, is then generally filtered to remove insoluble salts and the like which may have formed during the neutralization.

The resulting organic phase, which consists of a hydrocarbyl aromatic compound, a hydroxy aromatic compound, and a carbonyl compound, can, when desired, be fractionally distilled to remove a portion of some of the components in substantially pure form. For example, the mixture of cyclohexylbenzene, phenol, and cyclohexanone which results from the acid catalyzed cleavage of cyclohexylbenzene hydroperoxide in cyclohexylbenzene can be fractionally distilled to separate a portion of the cyclohexanone and of the cyclohexylbenzene.

It is within the scope of this invention to remove by suitable methods at least one of the components of the above described acid cleavage product mixture before the extractive distillation with a hydrocarbon as described herein. For example, cyclohexanone can be removed from a mixture of cyclohexylbenzene, phenol, and cyclohexanone by a suitable method such as extraction. The remaining mixture of cyclohexylbenzene and phenol can be separated by extractive distillation with a hydrocarbon solvent as described herein.

According to the instant invention, an extractive distillation is carried out by feeding a hydrocarbon solvent and the mixture to be separated to a continuously operating fractionation column, the point of introduction of the hydrocarbon solvent usually and preferably being above the point of introduction of the mixture to be separated.

The hydrocarbon solvent employed in the extractive distillation of the instant invention is a liquid under the conditions of operation and can be an alkane, aromatic, alkylaromatic, or cycloalkylaromatic hydrocarbon or mixtures thereof. In general, the boiling point of said hydrocarbon solvent will be higher than the boiling point of the hydrocarbyl aromatic compound present in the mixture to be separated. This will allow the separation of the hydrocarbon solvent and the hydrocarbyl aromatic compound by fractional distillation for recycling.

Specific examples of suitable hydrocarbon solvents include hexadecane, octadecane, heptadecane, tetradecane, biphenyl, p-dicyclohexylbenzene, m-dicyclohexylbenzene, 1,3,5-tricyclohexylbenzene, octylbenzene, 1,3,5-triethylbenzene, diphenylmethane, and mixtures thereof.

The extractive distillation conditions will be those suitable for the separation. Normally, the temperature within the fractionation column will be below about 150° C. to avoid undesirable side reactions of components of the mixture. The extractive distillation can be carried out at atmospheric pressure; although it is preferred to employ a reduced pressure.

The weight ratio of hydrocarbon solvent to mixture being fed to the fractionation column will be broadly in the approximate range of from about 0.05/1 to about 100/1, preferably from about 0.5/1 to about 10/1.

Referring to the drawing, the acid cleavage product mixture to be separated is introduced by line 1, via flowmeter 2, into the fractional distillation column 3. Hydrocarbon solvent is introduced by 4, via flowmeter 5, into column 3 at a point above the point of introduction of the acid cleavage mixture. An overhead fraction consisting of the hydroxy aromatic compound and the carbonyl compound is removed from column 3 by 6 and transferred to a suitable separation step.

The bottoms fraction containing the hydrocarbyl aromatic compound and the hydrocarbon solvent is withdrawn from the column 3 by 7 and introduced into a second fractional distillation column 8 where the hydrocarbyl aromatic compound is removed overhead by 9. The hydrocarbon is removed from column 8 as the bottoms fraction by 10 and sent to column 3 by rotameter 5 and 4. Additional hydrocarbon can be introduced into the system by 12 from reservoir 11 to compensate for losses of solvent.

The respective fractional distillations in columns 3 and 8 are preferably carried out under reduced pressure, applied by lines 13 and 14, respectively. The pressure will be adjusted by one skilled in the art in possession of this disclosure, having studied the same, to obtain optimum results depending upon the separation and the solvent selected. Ordinarily, the reduced pressure, when employed, will be of the order of about 50–150 millimeters of mercury.

When a mixture of a hydrocarbyl aromatic compound and a hydroxy aromatic compound is introduced into column 3 by line 1, the overhead fraction will consist of the hydroxy aromatic compound.

EXAMPLES

The following examples are presented to demonstrate operability of the instant invention. The abbreviation CHB is used in the examples to denote cyclohexylbenzene. The CHB used in the examples contained 1 to 2 wt % of other compounds such as methylcyclopentylbenzene and bicyclohexyl.

Extractive distillations were carried out in an apparatus which contained an electrically heated column [$\frac{3}{4}$" (19 mm) diameter×36" (914 mm) length] containing $\frac{1}{4}$" (6.4 mm) Por-Pak stainless steel perforated screen packing. The extraction solvent was fed through a rotameter and heated coil to a column inlet 3" (76 mm) from the top of the column. The mixture to be separated was fed through a rotameter and heated coil to a column inlet 18" (457 mm) from the top of the column. The overhead fraction was condensed and collected for analysis by gas-liquid chromatography (glc). The bottoms fraction was collected in a heated flask for glc analysis.

Fractional distillations were carried out in an apparatus which contained an electrically heated column [$\frac{3}{4}$" (19 mm) diameter×24" (610 mm) length] containing #3008 stainless steel Heli-Pak wire coils. Fractions were collected using a 10/1 reflux ratio and analyzed by glc.

The results as shown in Table I demonstrate that an extractive distillation of a mixture of CHB, phenol, and cyclohexanone with high boiling hydrocarbon solvents yield an overhead fraction that has very low or undetectable amounts of CHB.

Example I

A series of runs were conducted to demonstrate the separation of a mixture of CHB, phenol, and cyclohexanone by extractive distillation with hydrocarbon solvents. The conditions used and the results of analysis of the overhead fraction are shown in Table I. Analysis of the bottoms fractions by glc showed that CHB, the hydrocarbon solvent, and the phenol and cyclohexanone that did not go to the overhead fraction were present.

Most of the phenol and cyclohexanone in the original mixture was present in the overhead fraction and the actual amount in the overhead varied somewhat with the solvent/feed ratio (run 1 vs. run 2). The amount of hydrocarbon solvent present in the overhead fraction depends on the hydrocarbon boiling point (see run 11) and the fractionating ability of the column (run 2 versus run 3). Runs 16 and 17 show that more polar solvents (diphenyl phthalate and dibutyl phthalate) do not remove as much CHB from the mixture as hydrocarbon solvents. Thus, the solvents of the invention yielded distillate containing only of the order of 0.1, approximately, whereas the non-hydrocarbon solvents allowed ten or more times as much CHB to be in the distillate.

The above results demonstrate operability of the extractive distillation of the invention for the separation of CHB from a mixture of CHB, phenol, and cyclohexanone and demonstrate the advantages of hydrocarbon solvents over more polar solvents.

Example II

Another series of runs was conducted to demonstrate the separation of phenol and CHB by extractive distillation with a hydrocarbon solvent and the advantage of hydrocarbon solvents over polar solvents. The results of these runs are shown in Table II along with the conditions used.

Run 22, which used octadecane as solvent, gave a 100% phenol recovery. Very low amounts of CHB and solvent resulted in the overhead. Runs 18, 20, and 21 used polar solvents and gave lower phenol and high CHB levels in the overhead fractions. Run 19, which used a 80/20 mixture of dibutyl phthalate and octadecane as the solvent for extractive distillation, had a low CHB content, but still a relatively low phenol content in the overhead fraction.

The above results demonstrate operability of the instant invention for the separation of a mixture of CHB and phenol and the advantage of using hydrocarbon solvents rather than polar solvents in the extractive distillation.

Example III

A fractional distillation of a mixture of phenol, cyclohexanone, and CHB was carried out to illustrate the difficulties involved in separation of the above three components by fractional distillation. A solution containing 19.5 wt. % phenol, 19.5 wt % cyclohexanone, and 61 wt % CHB was fractionally distilled at a pressure of 127 mm. The results of a glc analysis of each of the fractions are shown in Table III.

TABLE I

| Run[a] | Solvent | Pressure, mm, Hg | Head Temp., °C. | Solvent/Feed Ratio | Distillate Analysis, wt. % | | | | Ketone & Phenol Recovered, wt. % |
|---|---|---|---|---|---|---|---|---|---|
| | | | | | Cyclohexanone | CHB | Phenol | Solvent | |
| 1 | Hexadecane | 100 | 122 | 3.0 | 24.8 | n.d.[i] | 68.8 | 4.4 | 97.3 |
| 2 | " | 100 | 122 | 1.1 | 26.4 | 0.02 | 69.7 | 3.8 | 92.4 |
| 3[b] | " | 100 | 123 | 1.8 | 27.7 | n.d. | 70.9 | 1.4 | 99.0 |
| 4[b] | " | 80 | 117 | 1.0 | 26.9 | 0.06 | 71.9 | 1.1 | 95.5 |
| 5[b,f] | " | 100 | 123 | 2.0 | 27.6 | 0.02 | 72.0 | 0.3 | 91.8 |
| 6 | " | 130 | 129 | 3.75 | 26.3 | n.d. | 68.6 | 4.99 | 100 |
| 7[b] | " | 80 | 115 | 2.5 | 26.8 | n.d. | 68.8 | 3.85 | 100 |
| 8 | [c] | 100 | 123 | 2.0 | 27.5 | 0.15 | 71.6 | t[e] | 97.6 |
| 9 | [c] | 100 | 122 | 2.9 | 27.6 | 0.04 | 72.0 | 0.3 | 97.0 |
| 10 [d] | [c] | 100 | 112 | 3.0 | 27.6 | 0.04 | 72.2 | 0.13 | 100 |
| 11 | Tetradecane | 100 | 123 | 3.1 | 25.0 | n.d. | 58.6 | 16.2 | 100 |
| 12 | Octadecane | 100 | 123 | 2.1 | 28.0 | 0.06 | 70.6 | 0.9 | 96 |
| 13[b] | " | 80 | 118 | 3.2 | 27.6 | n.d. | 72.3 | n.d. | 100 |
| 14[b,g] | " | 80 | 118 | 3.0 | 27.6 | n.d. | 72.3 | n.d. | 97.8 |
| 15 | " | 92 | 108 | 1.0 | 28.1 | 0.08 | 71.7 | 0.08 | not calc. |
| 16 | Diphenyl phthalate | 100 | 96 | 1.6 | 33.7 | 2.54 | 63.8 | n.d. | " |
| 17 | Dibutyl phthalate | 120 | 102 | 1.3 | 50.0 | 1.40 | 48.3 | n.d. | " |
| 3a[b,h] | Hexadecane | 100 | 122 | 1.0 | 27.2 | 0.10 | 71.2 | 1.4 | 97.1 |

[a]Feed = 68 wt % phenol, 27 wt % cyclohexanone, 5 wt % CHB except for run 14.
[b]An 8" (203 mm) extension was added to the top of the column.
[c]A mixture containing 85 wt % dicyclohexylbenzenes and 15 wt % tricyclohexylbenzenes; that is the heaviest fraction from the hydro-alkylation of benzene.
[d]Removed bottoms fraction from apparatus during the distillation.
[e]t = trace
[f]Lower heat on top portion of column.
[g]Feed = 2 wt % 1-phenylcyclohexene, 67 wt % phenol, 26 wt % cylohexanone, and 5 wt % CHB.
[h]Run 3a should be read after reading Run 3
[i]n.d. = not detected

TABLE II

| Run | Solvent | Pressure, mm, Hg | Head Temp., °C. | Solvent/Feed Ratio by volume | Distillate Analysis, wt. % | | | Phenol Recovery, wt. % |
|---|---|---|---|---|---|---|---|---|
| | | | | | CHB | Phenol | Solvent | |
| 18[a] | Dibutyl phthalate | 80 | 119 | 2.6 | 1.52 | 98.3 | n.d.[d] | 90.3 |
| 19[a] | Dibutyl phthalate (80%) Octadecane (20%) | 80 | 115 | 2.8 | 0.36 | 99.5 | n.d. | 88.2 |
| 20[b] | N-Cyclohexyl-2-pyrrolidinone | 120 | 128 | 3.5 | 22.7 | 75.3 | n.d. | 66.1 |
| 21[c] | N,N-Diethyl-dodecanamide | 50 | 95 | 2.6 | 1.26 | 98.6 | n.d. | 81.6 |

TABLE II-continued

| Run | Solvent | Pressure, mm, Hg | Head Temp., °C. | Solvent/Feed Ratio by volume | Distillate Analysis, wt. % | | | Phenol Recovery, wt. % |
|---|---|---|---|---|---|---|---|---|
| | | | | | CHB | Phenol | Solvent | |
| 22(c) | Octadecane | 50 | 99 | 2.4 | 0.07 | 99.4 | 0.5 | 100 |

(a)Feed: 81.4 wt. % Phenol, 9.0 wt. % CHB, 9.5 wt. % dibutyl phthalate
(b)Feed: 81 wt. % phenol, 9 wt. % CHB, 10 wt. % N-cyclohexyl-2-pyrrolidinone
(c)Feed: 90 wt. % phenol, 10 wt. % CHB
(d)n.d. = not detected

TABLE III

| Fraction | Head Temp., °C. | Weight, g | Amount of starting solution, wt. % | Fraction Composition | | |
|---|---|---|---|---|---|---|
| | | | | Cyclohexanone, wt. % | CHB, wt. % | Phenol wt. % |
| 1-5 | 48-99 | 32.9 | 9.9 | 100 | n.d.(b) | n.d. |
| 6 | 99-121 | 4.1 | 1.2 | 93.3 | 1.7 | 4.6 |
| 7 | 121-132 | 9.0 | 2.7 | 40.3 | 2.9 | 56.6 |
| 8-9 | 130-132 | 18.1 | 5.4 | 26.6-27 | 0.9-0.3 | 70.8-71.5 |
| 10-12 | 131-132 | 53.6 | 16.1 | 24.7 | 0.7-3.2 | 73.8-71.3 |
| 13 | 131 | 6.8 | 2.0 | 23.0 | 1.5 | 74.8 |
| 14 | 131 161 | 7.7 | 2.3 | 19.0 | 13.4 | 67.6 |
| 15 | 161-170 | 10.8 | 3.2 | 0.5 | 97.8 | 1.7 |
| 16-19 | 170-172 | 183.6 | 55.1 | t(a) | 99 | t |
| Pot residue | — | 5.2 | 1.6 | n.d. | n.d. | t |

(a)t = trace
(b)n.d. = not detected

Fractions 1-5 are essentially pure cyclohexanone and fractions 16-19 are essentially pure CHB. However, fractions 6-15 are mixtures of all three components of the starting mixture. These results show that a fractional distillation of a mixture containing phenol, cyclohexanone and large amounts of CHB (61 wt. % in this case) cannot separate reasonably completely all three components.

Example IV

Another fractional distillation was conducted on a mixture of CHB, phenol, and cyclohexanone that represents a mixture resulting from an initial treatment to remove part of the CHB from an acid catalyzed CHB hydroperoxide cleavage product. A solution containing 6% CHB, 47% phenol, and 47% cyclohexanone was fractionally distilled at a pressure of 125 mm. The first 4 fractions (23% of starting solution) were almost pure cyclohexanone and the other 10 fractions were mixtures of CHB, phenol, and cyclohexanone. Typical fraction compositions were 25-26 wt. % phenol, 73-75 wt. % cyclohexanone, and 0.2 to 0.4 wt. % CHB and related impurities such as methylcyclopentylbenzene and bicyclohexyl. While this fractional distillation did remove a considerable amount of CHB from the mixture, it did not achieve the purity of the overhead fractions of extractive distillations with hydrocarbon solvents of Table I, the 0.2 to 0.4 wt. % CHB here not comparing favorably with the 0.1 or considerably lower values of Table I.

An extractive distillation run using CHB heavies was not included in Table I. The bottoms fraction was removed several times during the extractive distillation and stable conditions were not achieved. The overhead fractions are similar to those of run #10. The CHB heavies used were essentially a mixture as appears in footnote (c) of Table I.

In the specific separation of cyclohexylbenzene from the hydrocarbon solvent, to obtain a best separation yielding solvent for efficient reuse, it is now preferred that the hydrocarbon boil above about 250° C. at atmospheric pressure.

It will be noted that the presence of a hydrocarbon solvent according to the invention, see Table II, runs 18 and 19, will materially improve the extraction in that the cyclohexylbenzene in the distillate is considerably reduced, i.e., 1.52 to 0.36 weight percent.

It is now preferred to employ hydrocarbon solvents which are substantially inert in the operation. However, in some cases, some reaction or modification of the solvent might take place and might even be beneficial. Thus, 100 percent purity of the hydrocarbon solvent is not always necessary.

Reasonable variation and modification are possible within the scope of the foregoing disclosure, the drawing and the appended claims to the invention the essence of which is that hydrocarbon solvent has been set forth as discovered to be outstandingly good for the separation of an acid catalyzed cleavage reaction mass obtained from an oxidized hydrocarbyl aromatic compound.

We claim:

1. A method for the continuous extractive distillation of a reaction mass obtained upon acid-catalyzed cleavage of the oxidation product of a hydrocarbyl aromatic compound, said mass containing said hydrocarbyl aromatic compound, which comprises conducting extractive distillation employing a hydrocarbon solvent having a boiling point higher than that of the hydrocarbyl aromatic compound and being a liquid under the conditions of the operation, by feeding said reaction mass into a distillation column at an intermediate point thereof, continuously introducing hydrocarbon solvent into said column at a point above the introduction of said reaction mass, but below the top of said column, taking off as overhead hydroxy aromatic compound and carbonyl compound, and continuously withdrawing hydrocarbyl aromatic compound and solvent as bottoms from said column.

2. A method according to claim 1 wherein the hydrocarbon solvent is selected from hexadecane, octadecane, heptadecane, tetradecane, biphenyl, p-dicyclohexylbenzene, m-dicyclohexylbenzene, 1,3,5-tricyclohexylbenzene, octylbenzene, 1,3,5-triethylbenzene, diphenylmethane, and mixtures thereof.

3. A method for the extractive distillation according to claim 1 wherein the materials being extractively distilled essentially comprise a hydrocarbyl aromatic compound, a hydroxy aromatic compound, and a carbonyl compound.

4. An extractive distillation according to claim 1 wherein the material being extractively distilled comprises cyclohexylbenzene, cyclohexanone and phenol.

5. A method according to claim 1 wherein the hydrocarbyl aromatic compound and hydroxy aromatic compound are respectively cyclohexylbenzene and phenol.

6. A method according to claim 1 wherein the solvent is hexadecane.

7. A method according to claim 1 wherein the solvent is selected from the solvents recited in claim 3.

8. A method according to claim 7 wherein the solvent selected is hexadecane.

* * * * *